United States Patent [19]

McDonald

[11] Patent Number: 5,217,464
[45] Date of Patent: Jun. 8, 1993

[54] THREE BAR CROSS ACTION LENS IMPLANTATION FORCEPS

[75] Inventor: Henry H. McDonald, 65 N. Madison, Suite 81, Pasadena, Calif. 91101

[73] Assignees: Henry H. McDonald; William W. Haefliger, both of Pasadena, Calif.; part interest to each

[21] Appl. No.: 890,810

[22] Filed: Jun. 1, 1992

[51] Int. Cl.⁵ .......................... A61B 17/28; B25B 9/02
[52] U.S. Cl. .................................. 606/107; 606/206; 606/207; 623/6; 294/99.2; 24/552; 81/419
[58] Field of Search ................... 623/6; 606/107, 205, 606/206, 207, 210; 294/1.2, 99.2; 24/551, 552, 553; 81/419, 420

[56] References Cited

U.S. PATENT DOCUMENTS

| | | | |
|---|---|---|---|
| 1,268,922 | 6/1918 | Bryan | 81/419 X |
| 3,611,842 | 10/1971 | Skipper | 294/99.2 |
| 3,741,602 | 6/1973 | Ploeckelmann | 606/210 X |
| 3,882,872 | 5/1975 | Douvas et al. | 606/107 |
| 4,198,980 | 4/1980 | Clark | 606/107 |
| 4,573,998 | 3/1986 | Mazzocco | 623/6 |
| 4,813,957 | 3/1989 | McDonald | 623/6 |
| 4,844,065 | 7/1989 | Faulkner | 606/107 |
| 4,957,505 | 9/1990 | McDonald | 623/6 |
| 4,959,070 | 9/1990 | McDonald | 623/6 |

FOREIGN PATENT DOCUMENTS

| | | | |
|---|---|---|---|
| 436232 | 7/1991 | European Pat. Off. | 606/107 |
| 52-14372 | 2/1977 | Japan | 294/99.2 |

Primary Examiner—Randall L. Green
Assistant Examiner—Mary Beth O. Jones
Attorney, Agent, or Firm—William W. Haefliger

[57] ABSTRACT

An apparatus for intraocular implantation of a plastic lens in the eye lens zone from which a natural lens has been removed via a surgical incision in the corneoscleral limbus comprising a surgical forceps having two arms and blades projecting beyond portions of the arms defining a cross-over locus, the blades clamping the plastic lens to be implanted; the blades including first and second spaced blades carried by one arm portion, and a third blade carried by the other arm portion, whereby stable three point support is provided for the lens during its passage through the incision into the eye.

12 Claims, 2 Drawing Sheets

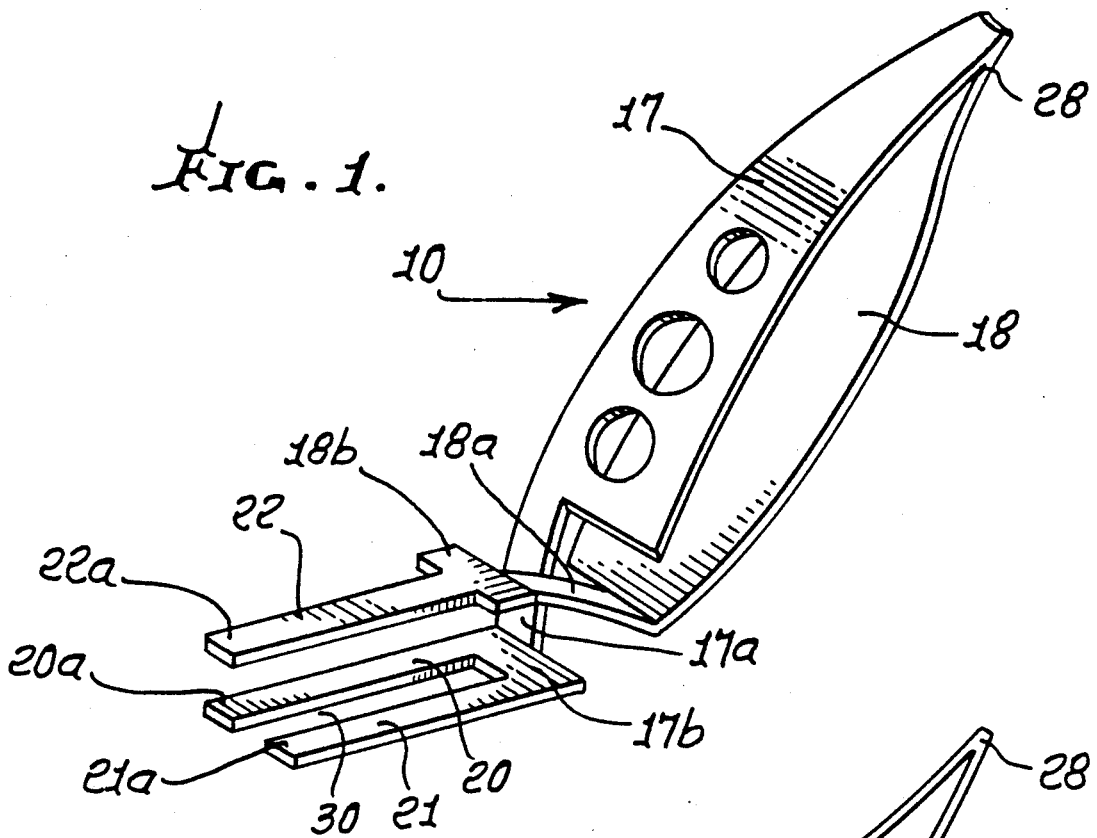
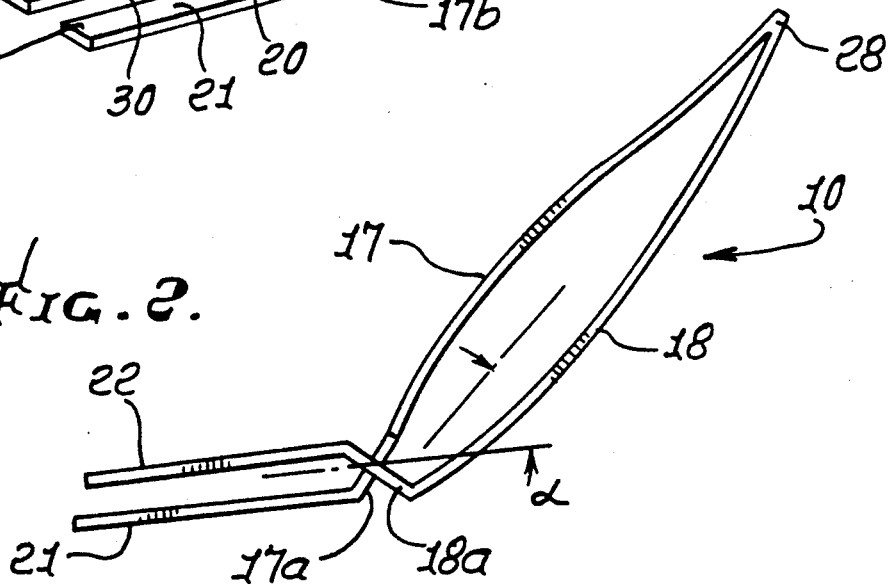
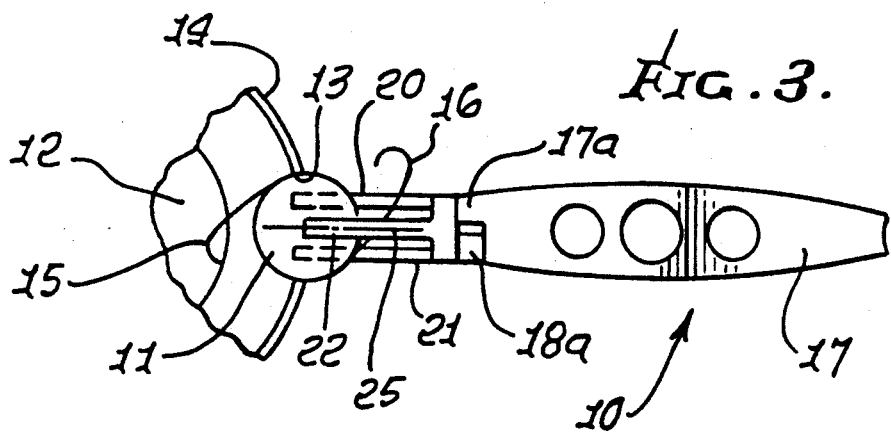

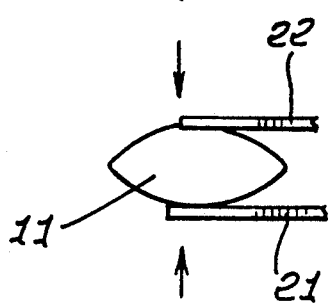
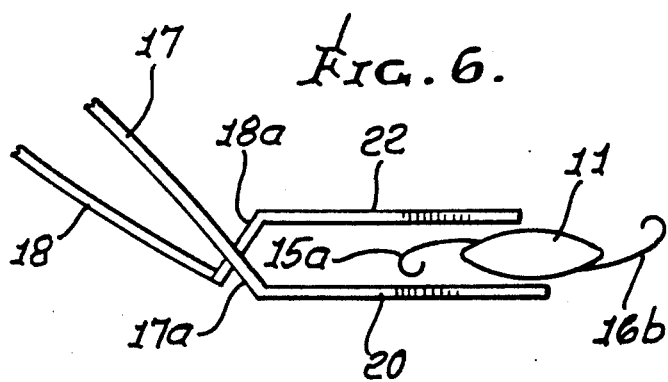
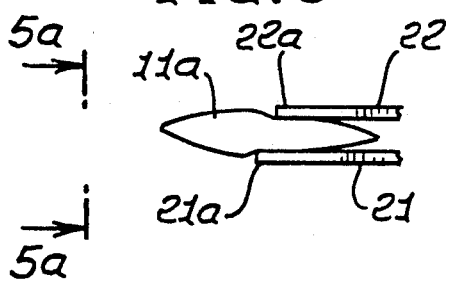
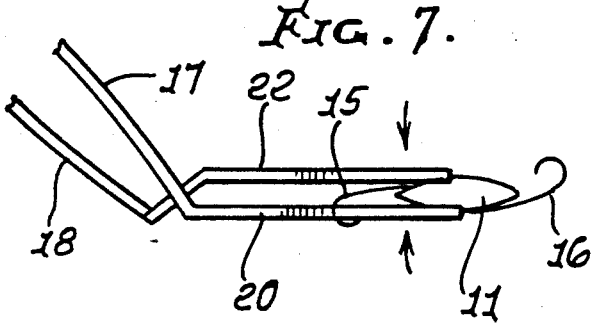
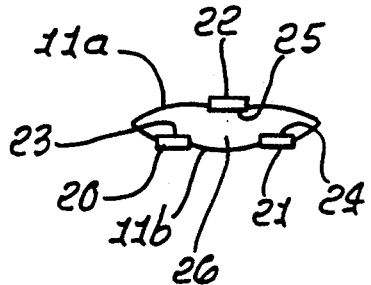
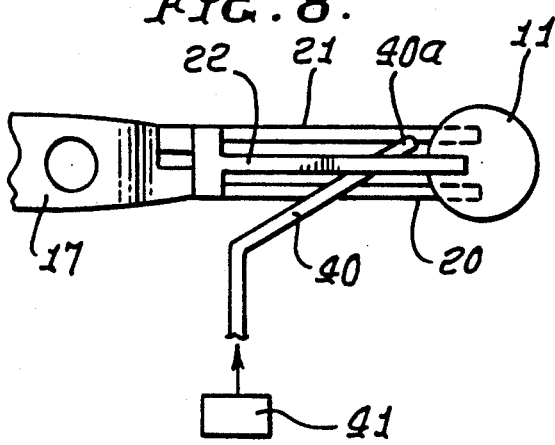

THREE BAR CROSS ACTION LENS IMPLANTATION FORCEPS

BACKGROUND OF THE INVENTION

This invention relates generally to intraocular lens implantation, and more particularly concerns apparatus and method for achieving such implantation, employing three blades.

In my U.S. Pat. No. 4,813,957, I have disclosed a method of implantation onto the eye of a plastic lens which has been folded, so as to pass through a very narrow incision in the corneosclera.

However, some surgeons do not desire to fold the soft lens implant, but prefer to implant the lens in unfolded condition. Also, if and when an inadvertent rupture of the posterior lens capsule occurs, the surgeon can avoid the use of an anterior chamber lens implant with al its potential complications by simply using a non-folded, soft lens implant through a small wound.

There is therefore need for an improved lens implantation forceps enabling easy grasping of a nonfolded plastic lens for passing it safely and accurately into the posterior chamber in the eye.

SUMMARY OF THE INVENTION

It is a major object of the invention to provide an improved lens implantation forceps to meet the above needs, enabling the surgeon to position lens haptics in secure areas of the sulcus, or in the lens capsular "bag". It should be emphasized that a ruptured posterior lens capsule will not permit the unfolding of the haptic without serious consequences.

It is another object of the invention to provide an improved lens implantation forceps that will enable safe insertion into the eye of a non-folded, soft lens implant, through a small surgical incision, the size of which can be less than 5 mm for a 6 mm or smaller lens implant, or with a "5 mm by 6 mm", or "4 mm by 6 mm" incision; and even a smaller width surgical wound, as with a "3 mm by 6 mm" soft lens implant passed through an incision 2.5 mm in width.

Basically, the apparatus of the invention is constructed for intraocular implantation of a plastic lens in the eye lens zone from which a natural lens has been removed via a surgical incision in the corneoscleral limbus, the apparatus comprising a) a surgical forceps having two arms, and blades projecting beyond portions of the two arms defining a cross-over locus, the blades clamping the plastic lens to be implanted, and in such manner that the blades follow the lens through the incision, b) the blades including first and second spaced blades carried by one arm portion, and a third blade carried by the other arm portion, providing three-point stable support for the lens.

As will be seen, the blades in the form of bars typically project forwardly, the third blade intersected by a plane bisecting the space between the first and second blades. The three blades extend in generally parallel relation; and the first and second blades have the same length, whereas the third blade is shorter, to embed its tip into the soft lens to help push it forward. This embedding prevents tips of the blade from sticking out and puncturing the posterior lens capsule over which it passes or injury to the endothelium. Also, three point support of the lens results in a high degree of maintained stability, as respects lens positioning relative to the forceps, during maneuvered passage through a narrow slit in the eye.

The blades or bars are integral with arms having portions that preferably define cross-over locations, as will be seen, whereby the lens implant is firmly held requiring no mental preoccupations and then permitting a very accurate-safe placement of the lens haptic and lens implant, without distraction.

The method of the invention includes the steps:

a) effecting clamping of the lens by the blades, so that the first and second blades engage one side of the lens and the third blade has a tip which deflects the lens inwardly at the opposite side thereof, and then manipulating the forceps to introduce the clamped plastic lens and the blades through the incision and into the eye interior, b) thereafter further manipulating the forceps to spread apart the blades within the eye, thereby releasing the plastic lens to accommodate to the eye zone, and thereafter relatively closing together the blades, c) and withdrawing the relatively closedtogether blades from the eye zone and via the incision.

These and other objects and advantages of the invention, as well as the details of an illustrative embodiment, will be more fully understood from the following specification and drawings, in which:

DRAWING DESCRIPTION

FIG. 1 is a perspective view of a lens implantation forceps incorporating the invention;

FIG. 2 is a reduced size side elevation showing the FIG. 1 forceps;

FIG. 3 is a reduced size top plan view of the FIG. 1 forceps;

FIG. 4 is a fragmentary side elevation showing initial grasping of a soft intraocular lens by means of the FIG. 1 forceps;

FIG. 5 is a view like FIG. 4 showing clamping of the lens by the three blades of the forceps;

FIG. 5a is a front view taken on lines 5a—5a of FIG. 5;

FIGS. 6 and 7 are additional side elevations showing initial and first grasping of a soft lens, with haptics; and FIG. 8 is an enlarged top plan view showing the position of an irrigation tube, extending between three blades.

DETAILED DESCRIPTION

In FIGS. 1-3, apparatus 10 is provided for intraocular implantation of a soft plastic lens 11 in the eye lens zone 12 from which a natural lens has been removed, such implantation involving insertion of the lens through a narrow slit 13 in the corneoscleral limbus 14. FIG. 3 shows the lens being inserted, with one haptic 15 preceding the other 16, as the lens is inserted.

The apparatus 10 includes upper and lower elongated arms 17 and 18 which are bowed away from one another, and extend at an approximate angle $\alpha$ relative to three forwardly extending and elongated blades 20–22 in the form of generally parallel flat bars. Angle $\alpha$ is greater than 30° and is typically about 40°. Two lower blades 20 and 21 are spaced below a single upper blade 22, so that the lens upper domed surface 11a is centally engaged by the blade 22, and the lens lower domed surface 11b is offset engaged by blades 20 and 21. See FIG. 5a. Stable three point support for the grasped lens is thereby provided, as at locations 23–25 seen in FIG. 5a.

Note the lower bulging extent 26 between blades 20 and 21, blocking rotation as well as lateral shifting of the lens; and also note the lower squeeze penetration of upper blade tip 22a into the lens upper domed surface, and upward squeeze penetration of lower blade tips 20a and 21a into the lens lower domed surface in FIG. 5, providing forward stability for resisting rearward sliding of the lens on the blades as the lens is maneuvered through the narrow slit, with interference fit. FIG. 4 shows the blade positions and lens configuration prior to squeezing of the lens between the upper and lower blades.

The blades are normally caused to close upon the lens with desired lens grasping force in response to spring effect of the arms; thus, arms 17 and 18 may be joined at 28, to provide cantilever spring effect. To controllably separate the upper blades relative to the lower blade, arms 17 and 18 are pressed toward one another, manually, allowing lens insertion between the blades, as in FIG. 4, and removal of the blades from a lens inserted into the eye. Note also the arm crossover portions 17a and 18a, which extend in side-by-side relation, in reverse angled relation to 17 and 18 respectively, whereby lower blades 20 and 21 are connected via 17a to upper arm 17, and upper blade 22 is connected via 18a to lower arm 18. Portion 17a is integral with a plate-like lateral support 17b for blade 22, and portion 18a is integral with a plate-like lateral support 18b for the two blades 20 and 21. Supports 17b and 18b remain above one another and define generally parallel planes, the plane of 18b also including upper blade 22; and the plane of 17b including the lower blades 20 and 21.

Blades 20 and 21 have the same lengths, to grasp the lens at opposite lateral sides of the dome crest, whereas blade 22 is of effective shorter length, i.e., its tip 22a is spaced rearwardly relative to the tips 20a and 21a of blades 20 and 21, as seen in FIGS. 1, 3 and 5. This causes the tip of blade 22 to squeeze penetrate the lens under surface 11b proximate the lower dome crest, assuring the existence of lens material forwardly of the lower blade tip so that rearward slippage of the lens relative to the blades is blocked, during insertion through the incision. Penetration of the tip or tips of the blade or blades into the lens in the manner and at the three point locations, as described, reduces the chance of blade caused injury to eye tissue.

Note the centered location of the blade 22 above and relative to the like first and second blades 20 and 21; thus, a vertical plane 41 extending forwardly and bisecting the space 30 between blades 20 and 21 passes centrally through the upper blade 22, bisecting the latter.

FIG. 6 shows rearward insertion of a lens 11, and its haptics 15a and 16b into position between the spread apart upper and lower blades. Relief of finger pressure on the arm 17 and 18 allows the blades to grasp the lens 11, as seen in FIG. 7, in preparation for insertion into the eye.

FIG. 8 shows an irrigation duct 40 positioned between the upper and lower blades, and terminating at 40a near the lens 11, to irrigate the latter, as during insertion into the eye. Saline aqueous solution may be passed through that duct, as from a source 41. The duct may be diametrically flexible, and sized to be grasped or squeezed by and between the upper and lower blades, while those arms also grasp the lens, as described. The duct then remains properly oriented for irrigation, during lens insertion.

The method of the invention includes the steps:
a) effecting clamping of the lens by the blades by manipulation of the forceps, including the arm portions, so that the first and second blades engage one side of the lens and the third blade has a tip which deflects the lens inwardly at the opposite side thereof, thereby to provide stable three point support for the lens, and then manipulating the forceps to introduce the clamped plastic lens and the blades through the incision and into the zone,
b) thereafter further manipulating the forceps to spread apart the blades, thereby releasing the plastic lens to accommodate to the zone, and thereafter relatively closing together the blades,
c) and withdrawing the relatively closedtogether blades from the zone and via the incision.

I claim:
1. An apparatus for intraocular implantation of a plastic lens in the eye lens zone from which a natural lens has been removed via surgical incision in the corneoscleral limbus, said apparatus comprising
a) a surgical forceps having two arms and blades projecting beyond portions of said arms defining a cross-over locus, the blades clamping the plastic lens to be implanted,
b) said blades including first and second spaced blades carried by one arm, and a third blade carried by the other arm, providing three-point stable support for the lens,
c) said blades extending in horizontal parallel planes, wherein each of said first, second and third blades has a longitudinal axis, a lateral width of each of said first, second and third blades with respect to said longitudinal axis being substantially equal, said arms extending upwardly and away from the blades in generally the same direction from said cross-over locus, said one arm extending above the other arm, said first and second blades extending in the same horizontal primary plane which is spaced below the horizontal secondary plane in which said third blade extends.

2. The apparatus of claim 1 wherein said blades extend forwardly in generally parallel direction, with the first and second blades extending forwardly to greater extents than the third blade.

3. The apparatus of claim 1 wherein the first and second blades have the same lengths.

4. The apparatus of claim 3 wherein the third blade has a length less than the lengths of the first and second blades.

5. The apparatus of claim 4 wherein said plastic lens has opposite sides, said first and second blades flatly engaging the plastic lens at one of said lens sides, the said third blade having a tip which deflects said lens inwardly at the other of said lens sides.

6. The apparatus of claim 1 wherein said arms have ends remote from said blades and which are joined at said ends.

7. The apparatus of claim 6 wherein said arms extend upwardly at angles greater than 30° relative to said horizontal planes of blades.

8. The apparatus of claim 1 including an irrigation duct extending between said third blade and said first and second blades, to supply irrigation liquid to a lens support zone defined by said blades.

9. The method of intraocular implantation of a plastic lens in the eye lens zone from which a natural lens has been removed via a surgical incision in the corneoscleral limbus, the method employing a surgical forceps having blades clamping the plastic lens to be implanted, said blades including first and second blades projecting horizontally beyond one portion of one arm and a third blade projecting horizontally beyond a second portion of a second arm, wherein each of said first, second and third blades has a longitudinal axis, the lateral width of each of said first, second and third blades with respect to said longitudinal axis being substantially equal, said arms projecting upwardly and away from the blades, one arm above the other, said method including the steps:

a) effecting clamping of the lens by the blades by manipulation of said forceps, including said arm portions, by variable squeezing of said arms so that said first and second blades engage first side of the lens and the third blade has a tip which deflects the lens inwardly at a second opposite side thereof, thereby to provide stable three point support for the lens, and then manipulating the forceps to introduce the clamped plastic lens and the blades through said incision and into said zone, b) thereafter further manipulating the forceps by increased squeezing together of said arms to spread apart the blades, thereby releasing the plastic lens to accommodate to said zone, and thereafter effecting relatively closing together the blades by decreased squeezing together of said arms, c) and withdrawing the relatively closed-together blades from said zone and via said incision.

10. The method of claim 9 wherein said arm portions define a cross-over locus, and including the step of maintaining said cross-over lens at or proximate said incision during said spreading apart of the blades and said closing together of the blades.

11. The method of claim 9 wherein each of said first and second sides of said lens has a dome shape, and said a) step of effecting clamping is effected to cause said first and second blades to engage said first side of the lens at opposite sides of said dome shape at said first side, and to cause said third blade to press inwardly the dome crest at the second side of the lens, whereby the blades are in endwise alignment with lens material which then precedes the blades into the incision.

12. The method of claim 9 including providing an irrigation duct and positioning said duct between the third blade and the first and second blades to terminate proximate said grasped lens, for irrigating the lens during passage thereof into the eye via said incision.

* * * * *